United States Patent [19]

Kaiser et al.

[11] Patent Number: 4,761,480
[45] Date of Patent: Aug. 2, 1988

[54] P-TOLUENE-SULFONYL-OXY SUBSTITUTED PYRIDINES

[75] Inventors: Carl Kaiser, Haddon Heights; Lawrence I. Kruse, Haddonfield, both of N.J.; Stephen T. Ross, Berwyn, Pa.

[73] Assignee: SmithKline Beckman Corporation, Philadelphia, Pa.

[21] Appl. No.: 916,132

[22] Filed: Oct. 7, 1986

Related U.S. Application Data

[62] Division of Ser. No. 761,936, Aug. 2, 1985, Pat. No. 4,634,711.

[51] Int. Cl.⁴ .......................................... C07D 213/65
[52] U.S. Cl. ................................. 546/294; 546/278; 546/295
[58] Field of Search ................................ 546/294, 295

[56] References Cited

U.S. PATENT DOCUMENTS 3,718,653 2/1973 Hamer .................................. 546/295

FOREIGN PATENT DOCUMENTS 0011460 5/1980 European Pat. Off. .

Primary Examiner—Jane T. Fan
Attorney, Agent, or Firm—Vincent L. Fabiano; Stuart R. Suter; Alan D. Lourie

[57] ABSTRACT

Potent dopamine-β-hydroxylase inhibitors having the Formula:

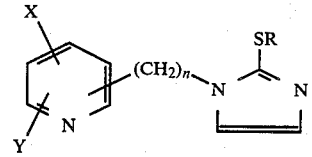

which are useful to inhibit dopamine-β-hydroxylase activity, pharmaceutical compositions including these inhibitors, and methods of using these inhibitors to inhibit dopamine-β-hydroxylase activity in mammals. Also disclosed are novel intermediates useful in preparing the presently invented inhibitors.

5 Claims, No Drawings

P-TOLUENE-SULFONYL-OXY SUBSTITUTED PYRIDINES

This is a division of application Ser. No. 761,936, filed Aug. 2, 1985, now U.S. Pat. No. 4,634,711.

FIELD OF THE INVENTION

This invention relates to novel compounds that inhibit dopamine-β-hydroxylase.

BACKGROUND OF THE INVENTION

In the catecholamine biosynthetic pathway, tyrosine is converted in three steps to norephinephrine (NE). Intermediates are dihydroxyphenylalanine (DOPA) and dopamine (DA). Dopamine is hydroxylated to norepinephrine by dopamine-β-hydroxylase (DBH) in the presence of oxygen and ascorbic acid.

Inhibition of catecholamine activity decreases blood pressure. Weinshilboum, *Mayo Clin. Proc.* 55, 39 (1980), reviews compounds that inhibit catecholamine activity by acting upon adrenergic receptors. Alternatively, the catecholamine biosynthetic pathway can be suppressed at any of the three steps, resulting in reduced NE levels. In addition to producing an antihypertensive effect, inhibitors of NE synthesis are active as diuretics, natriuretics, cardiotonics, and vasodilators. Inhibition of DBH activity can have the added advantage of increasing DA levels, which as reported by Ehrreich et al., "new Antihypertensive Drugs," Spectrum Publishing, 1976, pp. 409–432, has selective vasodilator activity at certain concentrations.

DBH inhibitors also have been shown to reduce or prevent formation of gastric ulcers in rats by Hidaka et al., "Catecholamine and Stress," edit. by Usdin et al., Permagon Press, Oxford, 1976, pp. 159–165 and by Osumi et al., *Japan J. Pharmacol.* 23, 904 (1973).

A number of DBH inhibitors are known. These generally are divided into two classes, namely, metal chelating agents, which bind to copper in the enzyme, and phenethylamine analogues. Rosenberg et al., "Essays in Neurochemistry and Neuropharmacology," Vol. 4, edit. by Youdim et al., John Wiley & Sons, 1980, pp. 179–192, and Goldstein, *Pharmacol. Rev.* 18 (1), 77 (1966), reivew DBH inhibitors. The former report that many potent DBH inhibitors have a hydrophobic side chain of size comparable to the aromatic ring of DA, leading the authors to suggest that incorporation of a terminal hydroxyl group on a 4- to 6-carbon side chain on a phenethylamine analogue may yield potent inhibitors.

Known DBH inhibitors include:

(a) 5-alkylpicolinic acids [See, Suda et al., *Chem. Pharm. Bull.* 17, 2377 (1969); Umezawa et al., *Biochem. Pharmacol.* 19, 35 (1969); Hidaka et al., *Mol. Pharmacol.* 9, 172 (1973); Miyano et al., *Chem. Pharm. Bull.* 26, 2328 (1978); Miyano et al., *Heterocycles* 14, 755 (1980); Claxton et al., *Eur. J. Pharmacol.* 37, 179 (1976)];

(b) BRL 8242 [See, Claxton et al., *Eur J. Pharmacol.* 37, 179 (1976)];

(c) 1-alkylimidazole-2-thiols [See, Hanlon et al., *Life Sci.* 12, 417 (1973); Fuller et al., *Adv. Enzyme Regul.* 15, 267 (1976)];

(d) substituted thioureas [See, Johnson et al., *J. Pharmacol. Exp. Ther.* 168, 229 (1969)]; and (e) benzyloxyamine and benzylhydrazine [See, Creveling et al., *Biochim. Biophys. Acta* 64, 125 (1962); Creveling et al., *Biochim. Biophys. Acta* 8, 215 (1962); Van Der Schoot et al., *J. Pharmacol. Exp. Ther.* 141, 74 (1963); Bloom, *Ann. N.Y. Acad. Sci* 107, 878 (1963)].

All the above compounds except benzyloxyamine and benzylhydrazine apparently owe their inhibitory effect to metal chelating properties. Alkyl derivatives of imidazole-2-thiol are more potent, presumably due to non-specific interaction of the alkyl substituent with the enzyme. Benzyloxyamine and benzylhydrazine are phenethylamine analogues which apparently act as competitive inhibitors.

In addition to the above compounds, Runti et al., *Il Farmaco Ed. Sci.* 36, 260 (1980), report that other fusaric acid derivatives and analogues inhibit DBH. These include phenylpicolinic acid, which has twice the inhibitory activity of fusaric acid, and 5-(4-chlorobutyl)picolinic acid, and others such as substituted amides of fusaric acid and acids and amides of 5-butyroylpicolinic acid, 5-aminopicolinic acid and 5-hydrazinopicolinic acid, and derivatives thereof.

Hidaka et al., *Molecular Pharmacology*, 9, 172–177 (1972) report that 5-(3,4-dibromobutyl)picolinic acid and 5-(dimethyldithiocarbamoyl)methylpicolinic acid are DBH inhibitors.

Bupicomide, 5-(n-butyl)picolinamine, is reported by Ehrreich et al., "New Antihypertensive Drugs", Spectrum Publications, 1976, pg. 409–432, to be a DBH inhibitor that has antihypertensive activity.

In European Patent Application No. 125,033 (published Nov. 14, 1984) a series of 1-phenyl and 1-phenylalkylimidazole compounds having a mercapto or alkylthio group in the 2-position are disclosed. These compounds are described as having DBH inhibiting activity.

U.S. Pat. No. 4,487,761 describes several methylpyridine derivatives isolated from the fermentation broth of a strain of Streptoverticillium. These compounds inhibit DBH activity.

Friedman et al., *Psychosomatic Med.* 40, 107 (1978), report that patients treated with alpha-methyl-DOPA, guanethidine, and reserpine, but not propranolol and diuretics, have lowered DBH levels, although the significance of the observation is uncertain.

Non-specific, often toxic effects of known DBH inhibitors have obviated clinical use of these compounds. Fusaric acid, for example, is hepatotoxic. See, for example, Teresawa et al., *Japan. Cir. J.* 35, 339 (1971) and references cited therein. Presumably, the picolinic acid structure interacts with a number of metalloproteins and enzymes non-specifically to produce the observed side effects.

In U.K. Patent Specification No. 1,155,580 are disclosed compounds having the formula:

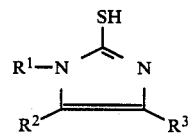

in which $R^2$ and $R^3$ can be H, and $R^1$ can be substituted phenyl. The compounds are said to have analgesic, anti-inflammatory and antipyretic properties. Gerbert et al., U.S. Pat. No. 3,915,980, disclose such compounds wherein $R^1$ can be phenyl or phen($C_{1-3}$)alkyl, as intermediates to imidazolyl-2-thioalkanoic acid esters.

Iverson, *Acta Chem. Scand.* 21, 279 (1967) reports compounds having the formula:

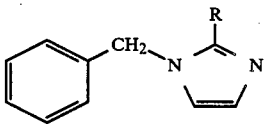

wherein R can be —CO$_2$H or —CH$_2$NHC$_6$H$_5$, but does not report pharmaceutical uses for the compounds.

SUMMARY OF THE INVENTION

The present invention resides in the discovery that DBH is inhibited by substituted 1-pyridylalkylimidazole-2-thiol and substituted 1-pyridylalkyl-2-alkylthioimidazole compounds. These compounds are potent and produce prolonged DBH inhibition.

Presently preferred compounds of the invention include:
1-(2'-pyridylmethyl)imidazole-2-thiol;
1-(3'-pyridylmethyl)imidazole-2-thiol;
1-(4'-pyridylmethyl)imidazole-2-thiol;
1-(3'-hydroxy-6'-pyridylmethyl)imidazole-2-thiol; and
1-(2'-hydroxy-5'-pyridylmethyl)imidazole-2-thiol.

In a further aspect of the invention there are provided novel intermediates useful in preparing hydroxy substituted 1-pyridylalkylimidazole-2-thiol and hydroxy substituted 1-pyridylalkyl-2-alkylthioimidazole compounds. Each of the intermediates is the p-toluene sulfonic acid ester of a substituted hydroxypyridine.

The invention also is a method of inhibiting DBH activity in mammals, including humans, which comrises administering internally to a subject an effective amount of a substituted 1-pyridylalkylimidazole-2-thiol or a substituted 1-pyridylalkyl-2-alkylthioimidazole compound.

Included in the present invention are pharmaceutical compositions comprising compounds useful in the method of the invention and a pharmaceutical carrier.

DETAILED DESCRIPTION OF THE INVENTION

The presently invented compounds that inhibit DBH have the following formula:

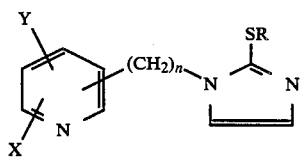

in which:
Y is hydrogen, hydroxy, halogen, or C$_{1-4}$ alkoxy;
X is hydrogen, halogen, halo C$_{1-4}$ alkyl, or any accessible combination thereof of up to three substituents;
n is 1-5; and
R is hydrogen or C$_{1-4}$ alkyl; or a pharmaceutically acceptable salt or hydrate thereof.

As used in Formula I, halo C$_{1-4}$ alkyl is defined to include halogenated alkyl substituents having from 1 to 4 carbon atoms and 1 to 5 halogen atoms. Examples of halo C$_{1-4}$ alkyls included in Formula I comprise trifluoromethyl and pentachloroethyl.

It is intended that Formula I include the tautomer of the compounds in which R is hydrogen, that is, compounds having the above formula wherein the imidazole moiety has either of the below formulae:

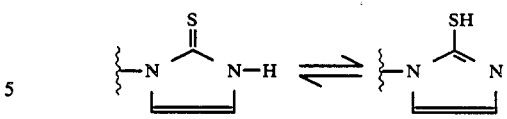

The compounds of Formula I are prepared from corresponding pyridyl aldehydes by known processes such as shown in Scheme I, below. The starting pyridyl aldehydes, except for hydroxypyridyl aldehydes, are known and described in published references or can be obtained readily.

Scheme I illustrates reductive amination of pyridyl aldehydes (A) having X and Y' substituents which are the same as X and Y in Formula I, except that Y' is not hydroxy, with an aminoacetaldehyde acetal followed by reduction by, for example, catalytic hydrogenation or treatment with a reducing agent such as NaBH$_4$, LiAlH$_4$, or AlH$_3$ to provide intermediate substituted pyridylamines (C). Upon reaction with hydrothiocyanic acid, the pyridylamines (C) yield imidazole-2-thiol products (D).

Scheme I

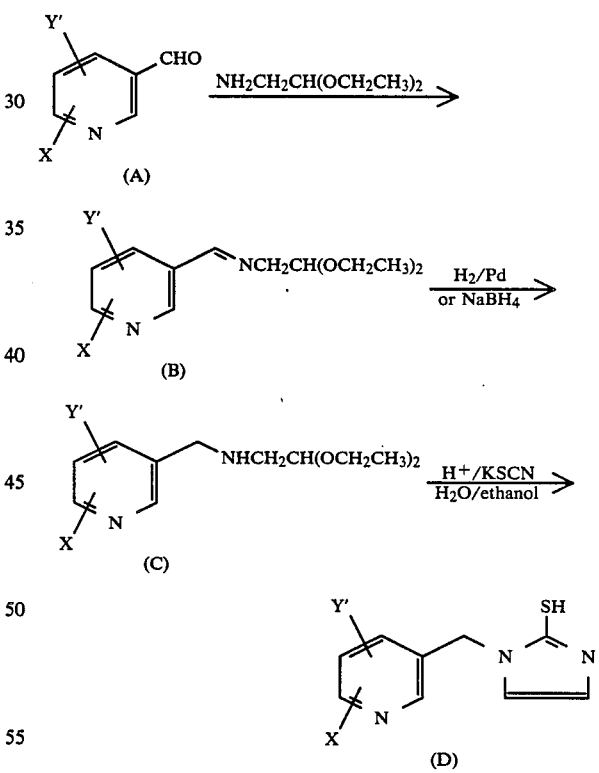

As illustrated in Scheme I, n is 1, however n can be from 1 to 5. The compounds wherein n is 2, 3, 4, or 5 preferably are prepared as described in Example 4, below. In the synthesis of these compounds, the process of Scheme I is employed except that the pyridyl aldehydes are replaced by pyridylalkyl aldehydes.

The compounds wherein R is a methyl group are prepared by alkylating corresponding imidazole-2-thiols with methyl iodide in methanol by known procedures. Other alkyl halides such as methyl bromide or methyl chloride can be substituted in an appropriate solvent for methyl iodide. Further, the compounds where R is an alkyl group other than methyl are prepared by reacting the corresponding imidazole-2-thiol with an alkyl halide, such a butyl iodide, to yield the desired 2-alkylthioimidazole compound of the invention.

A process for preparing hydroxypyridyl aldehydes was devised and employed in the preparation of presently invented hydroxypyridylimidazole-2-thiol compounds.

In preparing hydroxypyridyl aldehydes by the devised process, novel intermediate compounds of the following formula were synthesized:

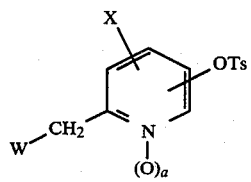

in which:

X is hydrogen, halogen, halo $C_{1-4}$ alkyl, or any accessible combination thereof of up to three substituents;

W is hydrogen, $C_{1-4}$ alkyl, acetoxy, propionyloxy or butyryloxy; and a is 0 or 1.

The novel process is depicted in Scheme II, in which X is the same as X in Formula I. As shown in Scheme II, known alkyl substituted hydroxypyridines (E), are used as the starting material. Initially, the hydroxy group is protected by reacting the hydroxypyridine (E) with p-toluenesulfonyl chloride to form the p-toluenesulfonate (F). Formation of the N-oxide compound (G) by reacting compound (F) with an oxidizing agent such as m-chloroperbenzoic acid, hydrogen peroxide, trifluoroperacetic acid, or peracetic acid is the next step and is followed by reacting the N-oxide compound (G) with an acyl anhydride or acyl halide to form an ester (H) by rearrangement. The pyridyl aldehyde (J) is formed by first hydrolyzing the ester (H) with triethylamine and ethanol to form an alcohol followed by oxidation to form a p-toluenesulfonate pyridyl aldehyde (J).

The p-toluenesulfonate pyridyl imidazole-2-thiol (K) is formed from the pyridyl aldehyde (J) by the process illustrated in Scheme I. Thereafter, Formula I compounds are prepared by alkaline hydrolysis of the p-toluenesulfonate pyridyl imidzaole-2-thiol to yield a hydroxypyridyl imidazole-2-thiol (L).

Scheme II

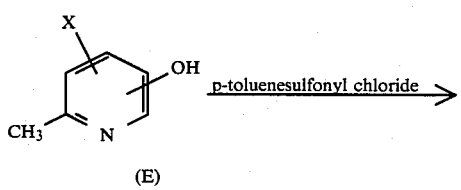

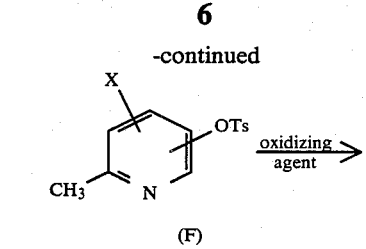

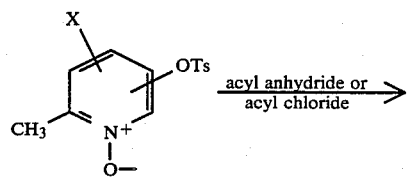

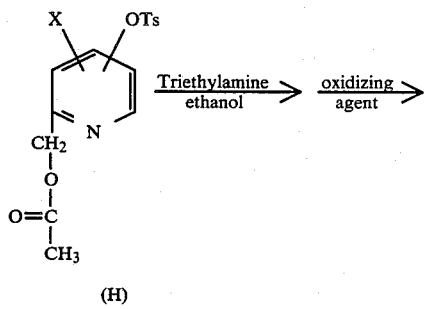

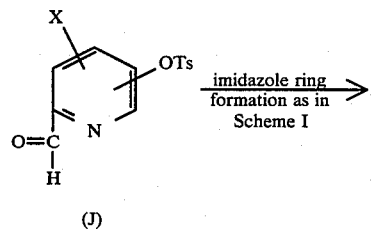

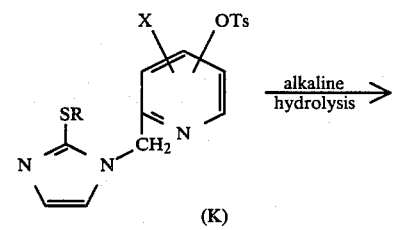

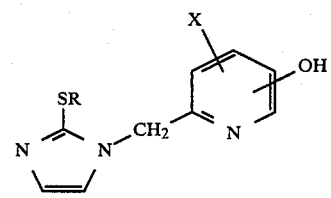

As exemplified in Example 10, below, it was found that starting 2-hydroxypyridine-5-carboxyaldehydes are preparable from corresponding 2-methoxypyridine-5-carboxaldehydes by known hydrolytic processes employing agents such as concentrated hydrobromic acid or boron tribromide. Once formed, the 2-hydroxypyridine-5-carboxaldehydes were employed as starting materials in a process analogous to Scheme I to form corresponding 1-(2'-hydroxypyridine-5'-alkyl)imidazole-2-thiols.

The pharmaceutically acceptable acid addition salts of the compounds of the invention are formed with strong or moderately strong organic or inorganic acids by methods known to the art. For example, the base is reacted with an inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

Because the compounds of Formula I inhibit DBH activity, they have therapeutic value as diuretic, natriuretic, cardiotonic, antihypertensive and vasodilator agents, as well as antiulcerogenic agents. Listed in Table I are the compounds of the invention that were tested for in vitro DBH inhibition by a standard procedure for assaying conversion of tyramine to octopamine in the presence of DBH. J. J. Pisano, et al., *Biochim. Biophys. Acta;* 43, 566–682 (1960). Octopamine was assayed following sodium periodate oxidation to p-hydroxybenzaldehyde by measuring spectrophotometric absorbance at 330 nm. In Table I, inhibition is given in molar concentration of compound at which DBH activity was halved ($IC_{50}$). Melting points (mp) are given in °C. Fusaric acid, by this test was found to have an $IC_{50}$ of $8 \times 10^{-7}$.

TABLE I

| Compound | mp | $IC_{50}$ |
|---|---|---|
| 1-(2'-pyridylmethyl)imidazole-2-thiol | 183–186° | $1.3 \times 10^{-4}$ |
| 1-(3'-pyridylmethyl)imidazole-2-thiol | 139–141° | $1.04 \times 10^{-4}$ |
| 1-(4'-pyridylmethyl)imidazole-2-thiol | 226–228° | $10^{-4}$ |
| 1-(3'-hydroxy-6'-pyridylmethyl)-imidazole-2-thiol | 255–260° (dec) | $2.7 \times 10^{-5}$ |
| 1-(2'-hydroxy-5'-pyridylmethyl)-imidazole-2-thiol | 251–256° (dec) | $10^{-4}$ |

Various compounds of the invention were tested for their effect in vivo on peripheral dopamine (DA) and norepinephrine (NE) levels substantially by the procedure of DaPrada and Zurcher, *Life Sciences,* 19, 1161, (1976). Groups of five spontaneously hypertensive rats were dosed orally, twice, the second dose approximately 18 hours after the first, and were sacrificed about 2 hours after the second dose. Averaged results, expressed in micrograms of DA and NE per gram of tissue are given in Table II.

TABLE II

| Compound | DA(ug/g) | NE(ug/g) | DA/NE Ratio |
|---|---|---|---|
| Control (Saline) | 0.246 | 6.65 | 0.0371 |
| Fusaric Acid 50 mg/kg | 0.653 (1) | 5.99 | 0.110 (1) |
| 1-(2'-pyridylmethyl)imidazole-2-thiol 50 mg/kg | 0.544 (2) | 6.08 | 0.0891 (2) |
| Control (Saline) | 0.309 | 6.87 | 0.0452 |
| Fusaric Acid 50 mg/kg | 0.552 (1) | 5.17 (1) | 0.107 (1) |
| 1-(3'-pyridylmethyl)imidazole-2-thiol 50 mg/kg | 0.425 (2) | 6.20 | 0.0688 (2) |
| Control (Saline) | 0.284 | 7.53 | 0.0377 |
| Fusaric Acid 50 mg/kg | 0.712 (1) | 6.70 | 0.106 (1) |
| 1-(4'-pyridylmethyl)imidazole-2-thiol 50 mg/kg | 0.396 (2) | 7.06 | 0.0561 (1) |

(1) $p < 0.001$
(2) $p < 0.01$

Further, spontaneously hypertensive rats were dosed with a suspension or solution of each of the compounds listed in Table II at a dose of 50 mg/kg intraperitoneally, and mean arterial blood pressure was monitored for 260 minutes using indwelling cannulae positioned in the tail arteries. In this study 1-(4'-pyridylmethyl-)imidazole-2-thiol was the most potent of the tested compounds. Approximate sixty percent reductions in blood pressure were observed fifteen minutes following administration of this compound. At 260 minutes after administration of this compound, blood pressure remained reduced by approximately forty percent when compared to vehicle-treated controls. Sustained blood pressure decreases of lesser magnitude were induced by each of the other tested compounds.

The compounds can be incorporated into convenient dosage forms such as capsules, tablets or injectable preparations. Solid or liquid pharmaceutical carriers can be employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or gylceryl distearate, alone or with a wax. The amount of solid carrier varies widely but, preferably, will be from about 25 mg to about 1 g per dosage unit. When a liquid carrier is used, the preparation will be in the form of a syrup, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating and compressing, when necessary, for tablet forms, or mixing, filling and dissolving the ingredients, as appropriate, to give the desired oral or parenteral products.

Doses of the present compounds in a pharmaceutical dosage unit will be an efficacious, nontoxic quantity selected from the range of 0.1–1,000 mg/kg of active compound, preferably 10–100 mg/kg. The selected dose is administered to a human patient in need of treatment from 1–6 times daily, orally, rectally, by injection, or continuously by infusion. Parenteral administration, which uses lower dosages is preferred. Oral administration, at higher dosages, however, also can be used when safe and convenient for the patient.

The following examples are illustrative of preparation of Formula I compounds. Example 11 illustrates preparation of the novel intermediates. The examples are not intended to limit the scope of the invention as defined hereinabove and as claimed below. All temperatures and melting points (mp) are given in degrees Celsius (°C.).

EXAMPLE 1

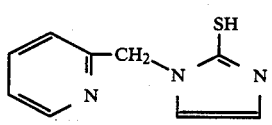

Freshly distilled pyridine-2-carboxaldehyde (10.7 g., 0.1 mole) was used as the starting material and, after mixture with aminoacetaldehyde diethyl acetal (13.3 g., 0.1 mole) was heated briefly to 50° and then dissolved in ethanol (150 ml.). The solution was stirred during the addition of sodium borohydride (3.8 g., 0.1 mole) and then stirred for approximately 12 hours. The resulting mixture was concentrated under vacuum and the residue was partitioned between water and ethyl acetate. The ethyl acetate extract was dried over anhydrous sodium sulfate and concentrated under vacuum to yield 18.9 g. of an oily amino intermediate which was heated at reflux with water (100 ml.), concentrated hydrochloric acid (20 ml.), and potassium thiocyanate (12.0 g). The solution was neutralized to pH 8 by the addition of sodium hydroxide and then cooled to 0°.

The mixture was filtered and the crystalline precipitate was purified by two recrystallizations from ethanol to yield 11.5 g. of 1-(2'-pyridylmethyl)imidazole-2-thiol, mp 183°–186°.

EXAMPLE 2

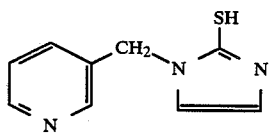

The process of Example 1 using pyridine-3-carboxaldehyde (10.7 g., 0.1 mole) as the starting material yielded, after recrystallization from ethanol, 12.8 g. of 1-(3'-pyridylmethyl)imidazole-2-thiol, mp 139°–141°.

Treatment of 1-(3'-pyridylmethyl)imidazole-2-thiol in ethanolic solution with a solution of hydrogen chloride in diethyl ether yields 1-(3'-pyridylmethyl)imidazole-2-thiol dihydrochloride.

EXAMPLE 3

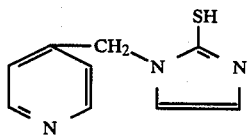

The process of Example 1 using pyridine-4-carboxaldehyde (10.7 g., 0.1 mole) as the starting material yielded, after recrystallization from ethanol, 9.7 g. of 1-(4'-pyridylmethyl)imidazole-2-thiol, mp 226°–228°.

EXAMPLE 4

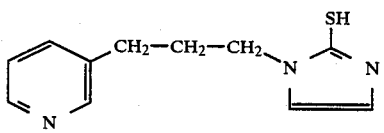

The process of Example 1 using 3-pyridinepropanal as the starting material yields 1-(3'-pyridylpropyl)imidazole-2-thiol.

EXAMPLE 5

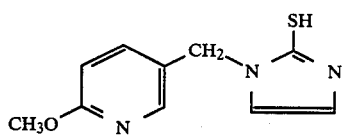

The process of Example 1 using 2-methoxy pyridine-5-carboxaldehyde (13.7 g., 0.1 mole) as the starting material yields 1-(2'-methoxy-5'-pyridylmethyl)imidazole-2-thiol.

EXAMPLE 6

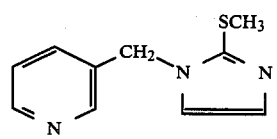

The reaction of 1-(3'-pyridylmethyl)imidazole-2-thiol with methyl iodine and sodium methoxide in methanol by known techniques yields 1-(3'-pyridylmethyl)-2-methylthioimidazole.

EXAMPLE 7

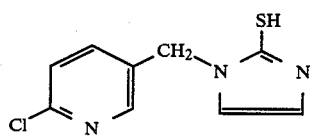

The process of Example 1 using 6-chloropyridine-3-carboxaldehyde as the starting material yields 1-(6'-chloro-3'-pyridylmethyl)imidazole-2-thiol.

EXAMPLE 8

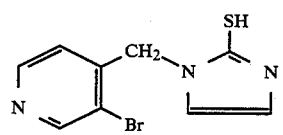

The process of Example 1 using 3-bromopyridine-4-carboxaldehyde as the starting material yields 1-(3'-bromo-4'-pyridylmethy)imidazole-2-thiol.

EXAMPLE 9

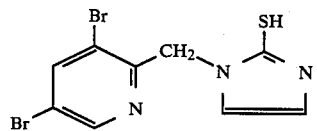

The process of Example 1 using 3,5-dibromopyridine-2-carboxaldehyde as the starting material yields 1-(3',5'-dibromo-2'-pyridylmethyl)imidazole-2-thiol.

EXAMPLE 10

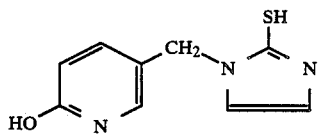

A mixture of 2-methoxypyridine-5-carboxaldehyde (Kompis, F. et al. *Eur. J. Med. Chem.*, 12, 531–36 (1977)) (12.7 g., 0.093 mole) and concentrated hydrobromic acid (127 ml.) was heated at reflux for 5 minutes, then cooled and concentrated under vacuum. The residue was triturated with diethyl ether to yield 3.95 g. of 2-hydroxypyridine-5-carboxaldehyde, mp 211°–215°.

Then, a mixture of 2-hydroxypyridine-5-carboxaldehyde, (7.4 g., 0.06 mole) and aminoacetaldehyde dimethyl acetal (6.3 g., 0.06 mole) in methanol (50 ml.) was warmed briefly, allowed to stand at 25° for approximately 12 hours, and then stirred at 0° during the addition of sodium borohydride (2.26 g., 0.06 mole). The solution then was stirred at 25° for one hour, diluted with water (20 ml), and concentrated under a vacuum. The resulting residue was dissolved in ethanol and filtered, and the filtrate was added to ethyl acetate. The resulting floculant precipitate was collected and dried to yield 3.2 g. of product as a tan solid.

The crude intermediate (6.3 g., 0.03 mole), produced above, and potassium thiocyanate (2.9 g., 0.03 mole) were heated at reflux in a mixture of water (36 ml.) and concentrated hydrochloric acid (9 ml.). After one hour, the mixture was cooled and concentrated, and the residue was suspended in ethanol and filtered. The filtrate was concentrated under a vacuum and resuspended in ethanol and filtered. This filtrate was concentrated, the residue was recrystallized from ethanol/acetonitrile, and triturated with water to yield 0.5 g. of 1-(2'-hydroxy-5'-pyridylmethyl)imidazole-2-thiol, mp 251°–256° (dec).

EXAMPLE 11

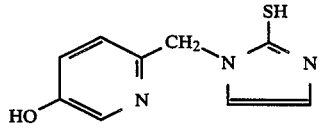

(i) Preparation of 3-hydroxy-6-methylpyridine 3-p-toluenesulfonate

A mixture of 3-hydroxy-6-methylpyridine (10.9 g., 0.1 mole), N,N-dimethylformamide (50 ml.), triethylamine (14.6 ml., 0.105 mole) and p-tuluenesulfonyl chloride (19.9 g. 0.10 mole) was heated at 100° and stirred for approximately 12 hours, and then poured into water (500 ml.). The solid product was recrystallized from diethyl ether/hexane to yield 21.0 g. of a white solid.

(ii) Preparation of 3-hydroxy-6-methylpyridine N-oxide 3-p-toluenesulfonate

A mixture of 3-hydroxy-6-methylpyridine 3-p-toluenesulfonate (21.0 g., 0.08 mole) in chloroform (150 ml.) was stirred as m-chloro perbenzoic acid (18.0 g., 0.104 mole) was added. After the initial exothermic reaction had subsided, the mixture was heated at reflux for one hour, then cooled and extracted three times with 20% aqueous sodium carbonate solution. The chloroform solution was dried over anhydrous $Na_2SO_4$, and concentrated to yield the desired intermediate as an oil which crystallized.

(iii) Preparation of 3-hydroxy-6-acetoxymethylpyridine 3-p-toluenesulfonate

A mixture of 3-hydroxy-6-methylpyridine-N-oxide 3-p-toluenesulfonate (18 g., 0.064 mole) in acetic anhydride (50 ml.) was heated at reflux for one hour and then cooled. Ethanol (150 ml.) was added cautiously, the solution was evaporated under vacuum, and the residue was redissolved in chloroform. The chloroform solution was extracted with 20% aqueous sodium carbonate solution, dried over anhydrous $Na_2CO_3$, and concentrated under vacuum. The dark oil was dissolved in ethyl acetate and purified by filtration through silica gel to yield the desired intermediate as a yellow oil.

(iv) Preparation of 3-hydroxy-6-hydroxymethylpyridine 3-p-toluenesulfonate

A solution of crude 3-hydroxy-6-acetoxymethylpyridine 3p-toluenesulfonate in methanol (100 ml.) and triethylamine (6 ml.) was heated at reflux for approximately 48 hours and then concentrated under vacuum. The crude residue was dissolved in ethyl acetate and washed twice with dilute hydrochloric acid, and the acidic washes were combined, neutralized with sodium hydroxide, and extracted twice with ethyl acetate. The ethyl acetate extracts were dried over anhydrous $Na_2SO_4$ and concentrated to yield 6 g. of product as a yellow oil.

(v) Preparation of 3-hydroxypyridine-6-carboxaldehyde 3-p-toluenesulfonate

A solution of crude 3-hydroxy-6-hydroxymethylpyridine 3-p-toluenesulfonate (6 g., 0.0215 mole) and chloroform (100 ml.) was treated with activated manganese dioxide (18 g.) and stirred at room temperature for approximately 60 hours. The mixture was filtered, and the filtrate was evaporated under vacuum. The crude residue was purified by silica gel chromatography using ethyl acetate/hexane as the eluant to yield 3.8 g. of product as a yellow solid.

(vi) Preparation of 1-(3'-hydroxypyridyl-6'-methyl)imidazole-2-thiol 3'-p-toluenesulfonate A solution of 3-hydroxypyridine-6-carboxaldehyde 3-p-toluenesulfonate (2.72 g., 0.0098 mole) and aminoacetaldehyde diethyl acetal (1.3 g., 0.0098 mole) in ethanol (25 ml.) was heated at reflux and then cooled and stirred during the addition of sodium borohydride (1 g.). After stirring at 25° for approximately 12 hours, the mixture was concentrated under a vacuum and the residue was partitioned between water and ethyl acetate. The ethyl acetate extract was evaporated to dryness, and the residue was treated for one hour at reflux with water (8.5 ml.), ethanol (4 ml.), concentrated hydrochloric acid (2 ml.) and potassium thiocyanate (1.02 g.). The mixture was cooled, diluted with water, and extracted with ethyl acetate. The ethyl acetate extracts were concentrated and purified by silica gel chromatography using ethyl acetate as the eluant to yield 1.64 g. of product as a white foam.

(vii) Preparation of 1-(3'-hydroxypyridyl-6'-methyl)imidazole-2-thiol

A mixture of 1-(3'-hydroxypyridyl-6'-methyl)imidazole-2-thiol 3'-p-toluenesulfonate (1.5 g., 4.16 mmol) in tetrahydrofuran (15 ml.) and 10% aqueous sodium hydroxide (6.5 ml.) was heated at reflux for one hour and cooled. The aqueous layer was treated with decolorizing charcoal, acidified to pH 7 with concentrated hydrochloric acid, and filtered. The crude solid precipitate was recrystallized from methanol to yield 0.3 g. (36%) of 1-(3'-hydroxypyridyl-6'-methyl)imidazole-2-thiol as tan crystals, mp 255°–260° (dec).

EXAMPLE 12

An oral dosage form for administering the presently invented compounds is produced by screening, mixing, and filling into a hard gelatin capsule the ingredients in Table III, below.

TABLE III

| Ingredients | Amounts |
| --- | --- |
| 1-(2'-pyridylmethyl)imidazole-2-thiol | 50 mg |
| magnesium stearate | 5 mg |
| lactose | 75 mg |

EXAMPLE 13

The sucrose, calcium sulfate dihydrate and pyridylimidazole shown in Table IV below, are mixed and granulated with a 10% gelatin solution. The wet granules are screened, dried, mixed with the starch, talc and stearic acid, screened and compressed into a tablet.

TABLE IV

| Ingredients | Amounts |
| --- | --- |
| 1-(3'-pyridylmethyl)imidazole-2-thiol | 100 mg |
| calcium sulfate dihydrate | 150 mg |
| sucrose | 20 mg |
| starch | 10 mg |
| talc | 5 mg |
| stearic acid | 3 mg |

EXAMPLE 14

1-(4'-pyridylmethyl)imidazole-2-thiol, 75 mg, is dispursed in 25 ml of normal saline to prepare an injectable preparation.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound having the formula:

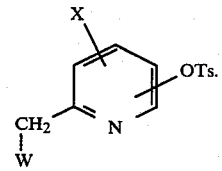

in which:
X is hydrogen, halogen, halo $C_{1-4}$ alkyl, or any accessible combination thereof of up to three substituents; and
W is acetoxy, propionyloxy, butyryloxy, or

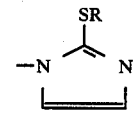

wherein R is hydrogen or $C_{1-4}$ alkyl.

2. A compound of claim 1 that is 3-hydroxy-6-acetoxymethylpyridine 3-p-toluenesulfonate.
3. A compound of claim 1 that is 3-hydroxy-6-hydroxymethylpyridine 3-p-toluenesulfonate.
4. A compound of claim 1 that is 3-hydroxypyridine-6-carboxaldehyde 3-p-toluenesulfonate.
5. A compound of claim 1 that is 1-(3'-hydroxypyridyl-6'-methyl)imidazole-2-thiol 3'-p-toluenesulfonate.

* * * * *